(12) United States Patent
Imran

(10) Patent No.: US 8,348,922 B2
(45) Date of Patent: Jan. 8, 2013

(54) METHOD AND APPARATUS FOR OSCILLATORY IONTOPHORETIC TRANSDERMAL DELIVERY OF A THERAPEUTIC AGENT

(75) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 242 days.

(21) Appl. No.: 12/658,637

(22) Filed: Feb. 10, 2010

(65) Prior Publication Data

US 2010/0331810 A1 Dec. 30, 2010

Related U.S. Application Data

(60) Provisional application No. 61/217,011, filed on May 23, 2009, provisional application No. 61/152,251, filed on Feb. 12, 2009, provisional application No. 61/214,642, filed on Apr. 25, 2009.

(51) Int. Cl.
*A61M 31/00* (2006.01)

(52) U.S. Cl. ........................................ 604/501

(58) Field of Classification Search ............ 604/20, 604/21, 501
See application file for complete search history.

(56) References Cited

U.S. PATENT DOCUMENTS

| | | | |
|---|---|---|---|
| 3,491,187 A | 1/1970 | Ely | |
| 4,325,367 A | 4/1982 | Tapper | |
| 4,731,049 A * | 3/1988 | Parsi | 604/20 |
| 4,734,090 A * | 3/1988 | Sibalis | 604/20 |
| 4,886,489 A | 12/1989 | Jacobsen et al. | |
| 5,310,404 A | 5/1994 | Gyory et al. | |
| 5,328,453 A * | 7/1994 | Sibalis | 604/20 |
| 5,385,543 A | 1/1995 | Haak et al. | |
| 5,503,632 A * | 4/1996 | Haak | 604/20 |
| 5,605,536 A | 2/1997 | Sibalis | |
| 5,693,024 A | 12/1997 | Flower | |
| 5,797,867 A | 8/1998 | Guerrera et al. | |
| 5,928,185 A | 7/1999 | Muller et al. | |
| 5,983,130 A | 11/1999 | Phipps et al. | |

(Continued)

FOREIGN PATENT DOCUMENTS

EP 0090425 A1 10/1983

OTHER PUBLICATIONS

Murhty et al., "Irontophoresis™: Transdermal Delivery of Iron by Iontophoresis," J. Pharm. Sci., 98(8): 2670-2676 (Aug. 2009).

(Continued)

*Primary Examiner* — Theodore Stigell
(74) *Attorney, Agent, or Firm* — Mahamedi Paradice Kreisman LLP

(57) ABSTRACT

Embodiments of the invention provide a device, system and method for the transdermal iontophoretic delivery of therapeutic agents. One embodiment provides a method comprising applying first and second patches to the skin. The first patch comprises a delivery electrode, a therapeutic agent and two lateral electrodes. The second patch comprises at least a delivery electrode. A first current is delivered to the skin and create a first driving force to transport the agent into the skin. A second current is delivered to the skin and creates a second driving force to oscillate the agent in a direction substantially parallel to the skin. The agent is transported across the skin using the first driving force to propel the agent into the skin, and the second driving force to oscillate the agent substantially parallel to the skin surface so that it is sieved through pathways of least diffusional resistance in the skin.

22 Claims, 11 Drawing Sheets

U.S. PATENT DOCUMENTS

| | | | |
|---|---|---|---|
| 6,019,877 | A | 2/2000 | Dupelle et al. |
| 6,064,908 | A | 5/2000 | Muller et al. |
| 6,330,471 | B1 | 12/2001 | Higo et al. |
| 6,512,950 | B2 | 1/2003 | Li et al. |
| 6,553,255 | B1 | 4/2003 | Miller et al. |
| 6,689,275 | B1 | 2/2004 | Gupta |
| 6,731,965 | B2 | 5/2004 | Menon et al. |
| 6,779,468 | B1 | 8/2004 | Gupta |
| 7,137,975 | B2 | 11/2006 | Miller et al. |
| 7,340,297 | B2 | 3/2008 | Tamarkin et al. |
| 7,375,139 | B2 | 5/2008 | Aldred |
| 7,437,189 | B2 | 10/2008 | Matsumura et al. |
| 7,496,401 | B2 | 2/2009 | Bernabei |
| 7,522,954 | B2 | 4/2009 | Tedoldi |
| 7,548,778 | B2 | 6/2009 | Roy |
| 7,558,625 | B2 | 7/2009 | Levin et al. |
| 7,590,444 | B2 | 9/2009 | Tanioka |
| 7,593,770 | B2 | 9/2009 | Lerner |
| 7,611,481 | B2 | 11/2009 | Cleary et al. |
| 7,816,404 | B2 | 10/2010 | McCall, Jr. |
| 2003/0060798 | A1 | 3/2003 | Fischer et al. |
| 2003/0199808 | A1 | 10/2003 | Henley et al. |
| 2004/0138646 | A1 | 7/2004 | Walla |
| 2005/0020487 | A1 | 1/2005 | Klaus et al. |
| 2005/0085751 | A1 | 4/2005 | Daskal et al. |
| 2005/0165393 | A1 | 7/2005 | Eppstein |
| 2005/0209565 | A1 | 9/2005 | Yuzhakov |
| 2005/0213286 | A1 | 9/2005 | Michel et al. |
| 2005/0238704 | A1 | 10/2005 | Zumbrunn et al. |
| 2005/0273046 | A1 | 12/2005 | Kwiatkowski et al. |
| 2006/0025715 | A1* | 2/2006 | Henley et al. ............. 604/20 |
| 2006/0216339 | A1 | 9/2006 | Ambron et al. |
| 2006/0229549 | A1 | 10/2006 | Hause et al. |
| 2006/0258973 | A1 | 11/2006 | Volt |
| 2007/0065521 | A1 | 3/2007 | Venkataraman et al. |
| 2007/0066934 | A1 | 3/2007 | Etheredge et al. |
| 2007/0083185 | A1 | 4/2007 | Carter |
| 2007/0083186 | A1 | 4/2007 | Carter et al. |
| 2007/0224253 | A1 | 9/2007 | Franklin |
| 2008/0027369 | A1 | 1/2008 | Carter et al. |
| 2008/0058699 | A1 | 3/2008 | Hause et al. |
| 2008/0058700 | A1 | 3/2008 | Hause et al. |
| 2008/0081051 | A1 | 4/2008 | Sabin et al. |
| 2008/0114282 | A1 | 5/2008 | Carter |
| 2008/0154178 | A1 | 6/2008 | Carter et al. |
| 2008/0287497 | A1 | 11/2008 | Anderson et al. |
| 2009/0036821 | A1 | 2/2009 | Lai |
| 2009/0062720 | A1 | 3/2009 | Anderson et al. |
| 2009/0124572 | A1 | 5/2009 | Nelson |
| 2009/0163597 | A1 | 6/2009 | Goto et al. |
| 2009/0171313 | A1 | 7/2009 | Yamamoto et al. |
| 2009/0221985 | A1 | 9/2009 | Bukshpan et al. |
| 2009/0254018 | A1 | 10/2009 | Nakayama |
| 2009/0259176 | A1 | 10/2009 | Yairi |
| 2009/0281475 | A1 | 11/2009 | Nisato et al. |
| 2009/0299264 | A1 | 12/2009 | Matsumura et al. |
| 2009/0299267 | A1 | 12/2009 | Durand |
| 2010/0204637 | A1 | 8/2010 | Imran |
| 2010/0331759 | A1 | 12/2010 | Imran |
| 2010/0331811 | A1 | 12/2010 | Imran |
| 2011/0082411 | A1* | 4/2011 | Imran ............. 604/20 |

OTHER PUBLICATIONS

International Search Report, Written Opinion and Notice of Transmittal of Same mailed Sep. 27, 2010 in PCT/US2010/023112.

International Search Report, Written Opinion and Notice of Transmittal of Same mailed Sep. 27, 2010 in PCT/US2010/023744.

Non-Final Office Action mailed Apr. 8, 2011 in U.S. Appl. No. 12/537,243.

International Search Report, Written Opinion and Notice of Transmittal of Same mailed Jun. 24, 2011 in PCT/US2010/051541.

International Preliminary Report on Patentability mailed Aug. 25, 2011 in PCT/US2010/023744.

International Preliminary Report on Patentability mailed Aug. 25, 2011 in PCT/US2010/023112.

International Search Report, Written Opinion and Notice of Transmittal of Same mailed Feb. 25, 2011 in PCT/US2010/040109.

Final Office Action mailed Oct. 28, 2011 in U.S. Appl. No. 12/537,243.

Notice of Allowance mailed Jan. 19, 2012 in U.S. Appl. No. 12/537,243.

International Preliminary Report on Patentability mailed Jan. 12, 2012 in PCT/US2010/040109.

International Preliminary Report on Patentability as issued in related International application PCT/US2010/051541, dated Apr. 19, 2012.

Non-final Office Action mailed in U.S. Appl. No. 12/824,147, dated Jun. 1, 2012.

Non-final Office Action mailed in U.S. Appl. No. 12/824,146, dated Jun. 1, 2012.

* cited by examiner

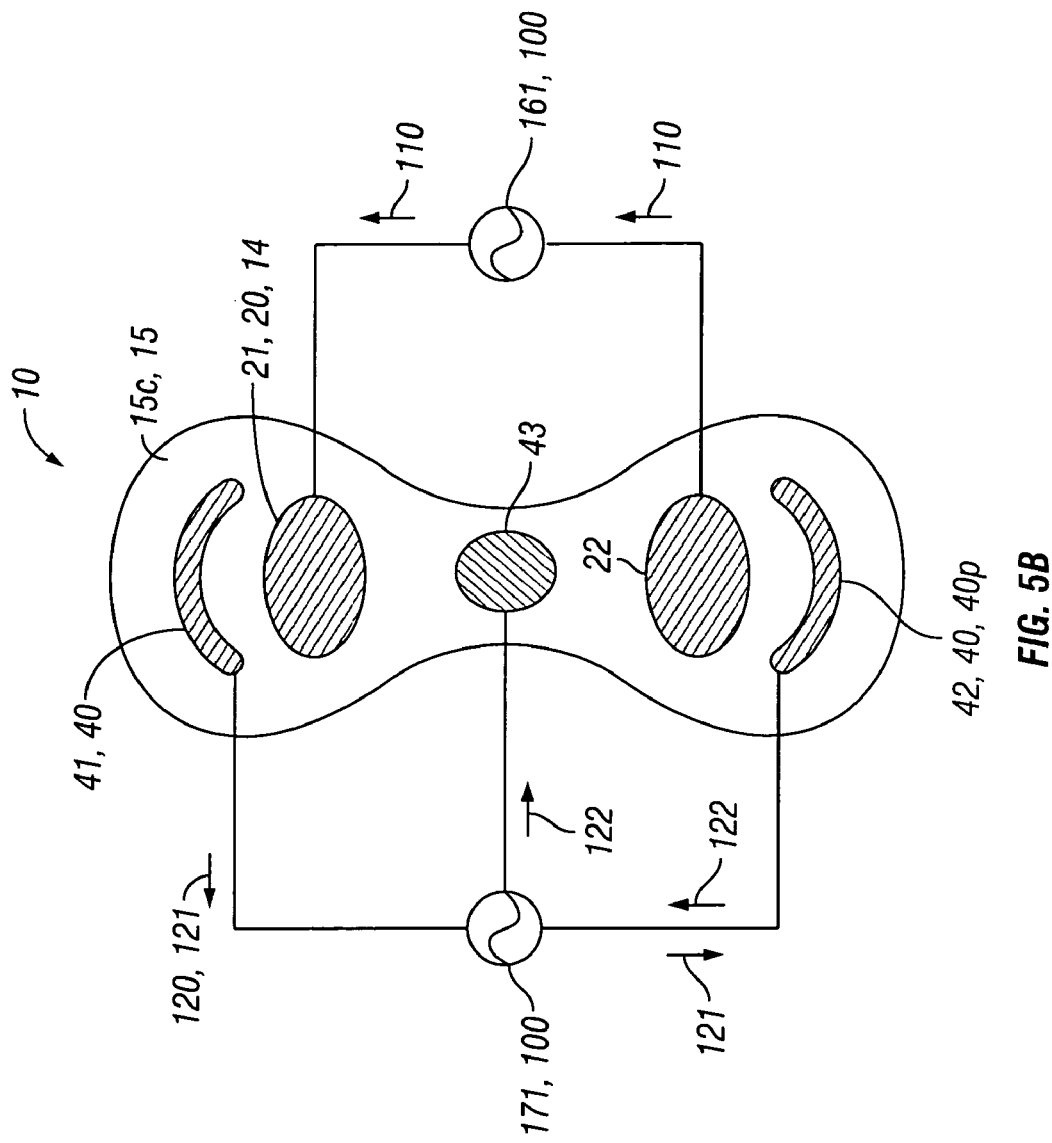

METHOD AND APPARATUS FOR OSCILLATORY IONTOPHORETIC TRANSDERMAL DELIVERY OF A THERAPEUTIC AGENT

RELATED APPLICATIONS

This application claims benefit of priority to Provisional U.S. Patent Application No. 61/217,011, entitled "Method and Apparatus for Oscillatory Iontophoretic Transdermal Delivery of a Therapeutic Agent", filed May 23, 2009; the aforementioned priority application being hereby incorporated by reference for all purposes.

This application also claims benefit of priority to Provisional U.S. Patent Application No. 61/152,251, entitled "Kit, System and Method for Transdermal Iontophoretic Delivery of Therapeutic Agents", filed Feb. 12, 2009; the aforementioned priority application being hereby incorporated by reference for all purposes.

This application also claims benefit of priority to Provisional U.S. Patent Application No. 61/214,642, entitled "Method For Transdermal Iontophoretic Delivery Of Chelated Agents", filed Apr. 25, 2009; the aforementioned priority application being hereby incorporated by reference for all purposes.

FIELD OF THE INVENTION

Embodiments described herein relate to transdermal delivery of various therapeutic agents. More specifically, embodiments described herein relate to oscillatory iontophoretic transdermal delivery of various therapeutic agents.

BACKGROUND

Iron and other micro nutrient deficiencies are a world-wide health problem, particularly in the undeveloped countries where it is a key underlying factor in impaired mental development in children. Iron deficiency alone affects over 3 billion people in the Third World and is blamed for 100,000 maternal deaths during childbirth each year as well as 134,000 deaths amongst children. Iron and other related micronutrient deficiencies are co-morbid with a variety of parasitic infections rampant in the Third World including hookworm, roundworm, malaria, amebiasis, giardiasis, schistosomiasis, leishmaniasis, etc.

The typical form of treatment for iron deficiency includes oral or intravenous drug delivery with various ferrous compounds. However, both oral and intravenous forms of drug delivery for treatment of anemia have a number of limitations. Oral delivery has poor absorption particularly in the presence of other medications as well as a number of side effects including cramping and diarrhea which resulting in up to 30% of patients discontinuing medication. Intravenous limitations include the requirement to mix and store the medication in liquid form as well as the use of sterile technique in administration. These can be particularly problematic in third world countries where adequate refrigeration and sterile needles are not readily available, limiting shelf life and exposing the patient to infection. Also, IV administration can include several risk factors including anaphylaxis and cardiovascular complications. Thus, there is a need for improved methods of drug delivery for the treatment of anemia and other medical conditions which can extend shelf life and are more easily used in settings lacking refrigeration or sterile medical supplies.

BRIEF SUMMARY

Embodiments described herein provide a device, system and method for the transdermal iontophoretic delivery of therapeutic agents. Many embodiments provide a device, system and method for the iontophoretic transdermal delivery of therapeutic agents using electrical currents to cause oscillatory motion of the therapeutic agent within the skin. Such embodiments can be utilized for the delivery of a number of therapeutic agents including the delivery of iron containing compounds for treatment of anemia and anemia related conditions.

One embodiment provides a method for the iontophoretic transdermal delivery of a therapeutic agent. The method comprises applying a first and second patch to the skin of a person in need of the therapeutic agent. The first patch comprises a delivery electrode, a therapeutic agent and two lateral electrodes. The second patch comprises at least a delivery electrode and may also include lateral electrodes. A first current is delivered to the skin, the first current flowing between the delivery electrodes and creating a first electromotive driving force to transport the therapeutic agent into the skin. Also, a second current is delivered to the skin, the second electric current flowing between the lateral electrodes of the first patch and creating a second electromotive driving force to oscillate the therapeutic agent in a direction substantially parallel to the skin surface and/or non-parallel to the direction of the first driving force. The therapeutic agent is transported across the skin using the first electromotive driving force to propel the agent into the skin, and the second electromotive driving force to oscillate the therapeutic agent substantially parallel to the skin surface and/or substantially non-parallel to the direction of the first driving force so that it is sieved through pathways of least diffusional resistance in the skin.

In many embodiments, the first current is an alternating current so that the therapeutic agent can be delivered from both patches. However, use of direct current is also contemplated for the first current. Also in many embodiments, the second current is an alternating current so that the electromotive driving force changes direction with each change in direction of the first current so as to produce the oscillating motion of the therapeutic agent (the agent having an ionic charge that is repelled or attracted by the second electromotive driving force). In various embodiments, the frequency of the second current can be in the range of 50 to 1 kHz with specific embodiments of 100, 250, 500 and 750 Hz. The frequency of the second current can also be adjusted depending upon one or more factors so as to enhance the oscillating motion of the therapeutic agent and in turn its transport through the skin using sieving motion. Such factors can include the frequency of the first current, the charge to mass ratio of the therapeutic agent, the conductive properties of the skin (e.g., impedance) and the type and thickness of the skin subjacent the patch(s).

In embodiments where the second patch contains lateral electrodes and is used to deliver therapeutic agent, a third current can be delivered from lateral electrodes on the second patch to create a third electromotive driving force to oscillate the therapeutic agent substantially parallel to the skin surface underneath the second patch and/or substantially non-parallel to the direction of the first driving force.

Another embodiment provides the following method for the iontophoretic transdermal delivery of a therapeutic agent. The method comprises delivering a first current to the skin to create a first electromotive driving force to transport the therapeutic agent into the skin, and delivering a second current to the skin to create a second electromotive driving force to oscillate the therapeutic agent in a direction substantially parallel to the skin surface. The therapeutic agent is transported across the skin using the first electromotive driving force to propel the agent into the skin, and the second electromotive driving force to oscillate the therapeutic agent substantially parallel to the skin surface so that it is sieved through pathways of least diffusional resistance in the skin. Additionally, the second driving force can be configured to oscillate the therapeutic agent in any direction substantially non-parallel to the direction of the first driving force to produce a sieving motion/action through the skin. The pathways of least diffusional resistance can include areas of greater hydration, reduced thickness, pores (e.g., sweat pores), hair follicles or gaps in the skin including gaps in the stratum corneum layer of the dermis.

In exemplary aspects, embodiments of the above method can be used to deliver various iron containing compounds including iron salts such as ferric chloride, as well as ferric pyrophosphate, ferric ammonium citrate and other chelated iron containing compounds. In the later cases, the method can be configured to deliver the ferric pyrophosphate or other chelated iron containing compound without any substantial cosmetic change to the skin such as a tattoo or other marking of the skin. In other exemplary aspects, embodiments of the above methods can be used for the delivery of various proteins, polypeptides and small molecules.

Further details of these and other embodiments and aspects of the invention are described more fully below, with reference to the attached drawing figures.

BRIEF DESCRIPTION OF THE DRAWINGS

FIG. 5b is a top view showing an embodiment of the invention having a single patch including two delivery electrodes with a lateral electrode on the side of each delivery electrode and a common lateral electrode located between the delivery electrodes.

DETAILED DESCRIPTION OF THE INVENTION

Figure 1:
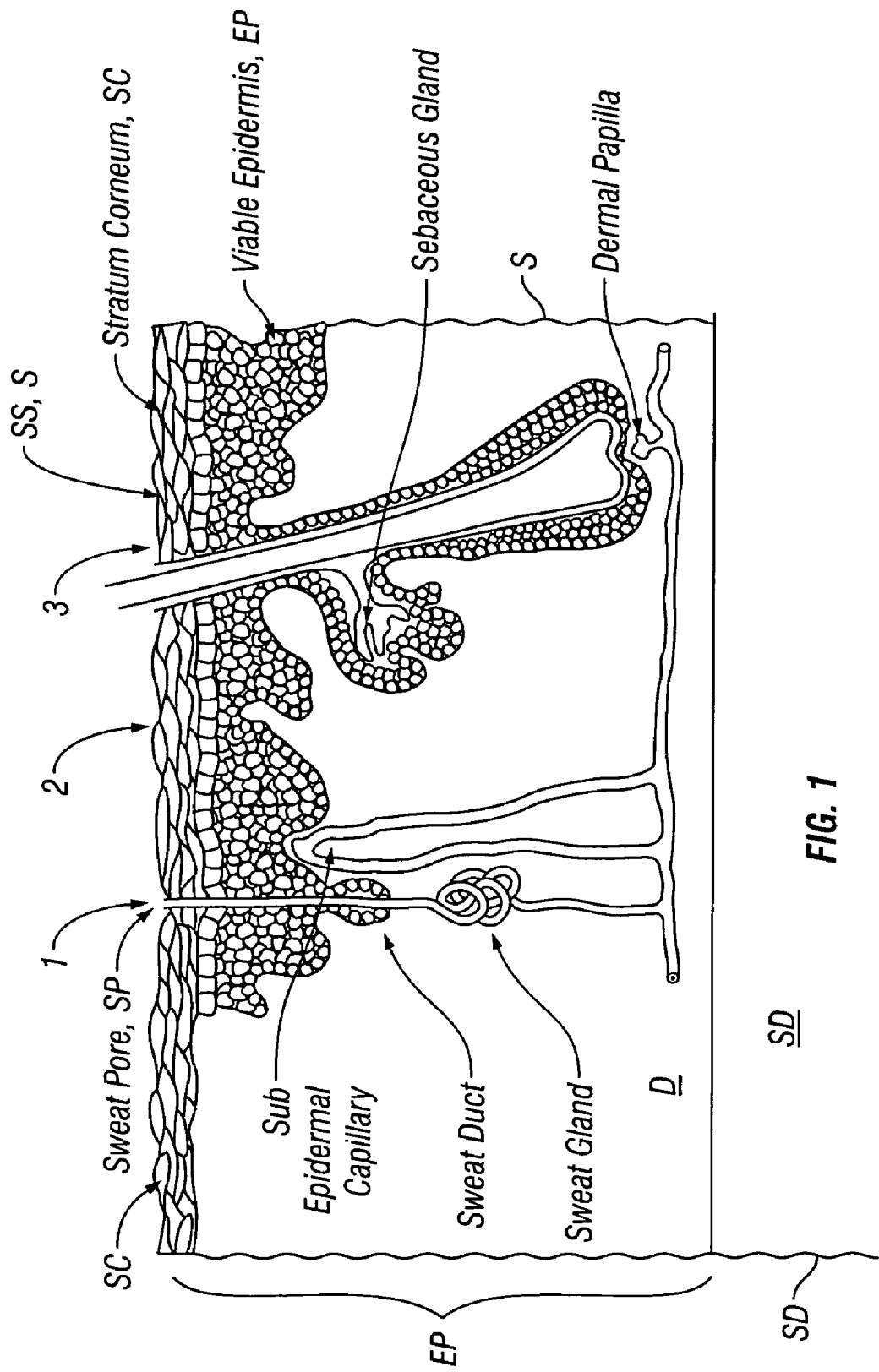
FIG. 1 is a cross sectional view showing the three main layers of the skin, the epidermis, the dermis and subcutaneous tissue as well as the passageways into the skin.
Figure 2:
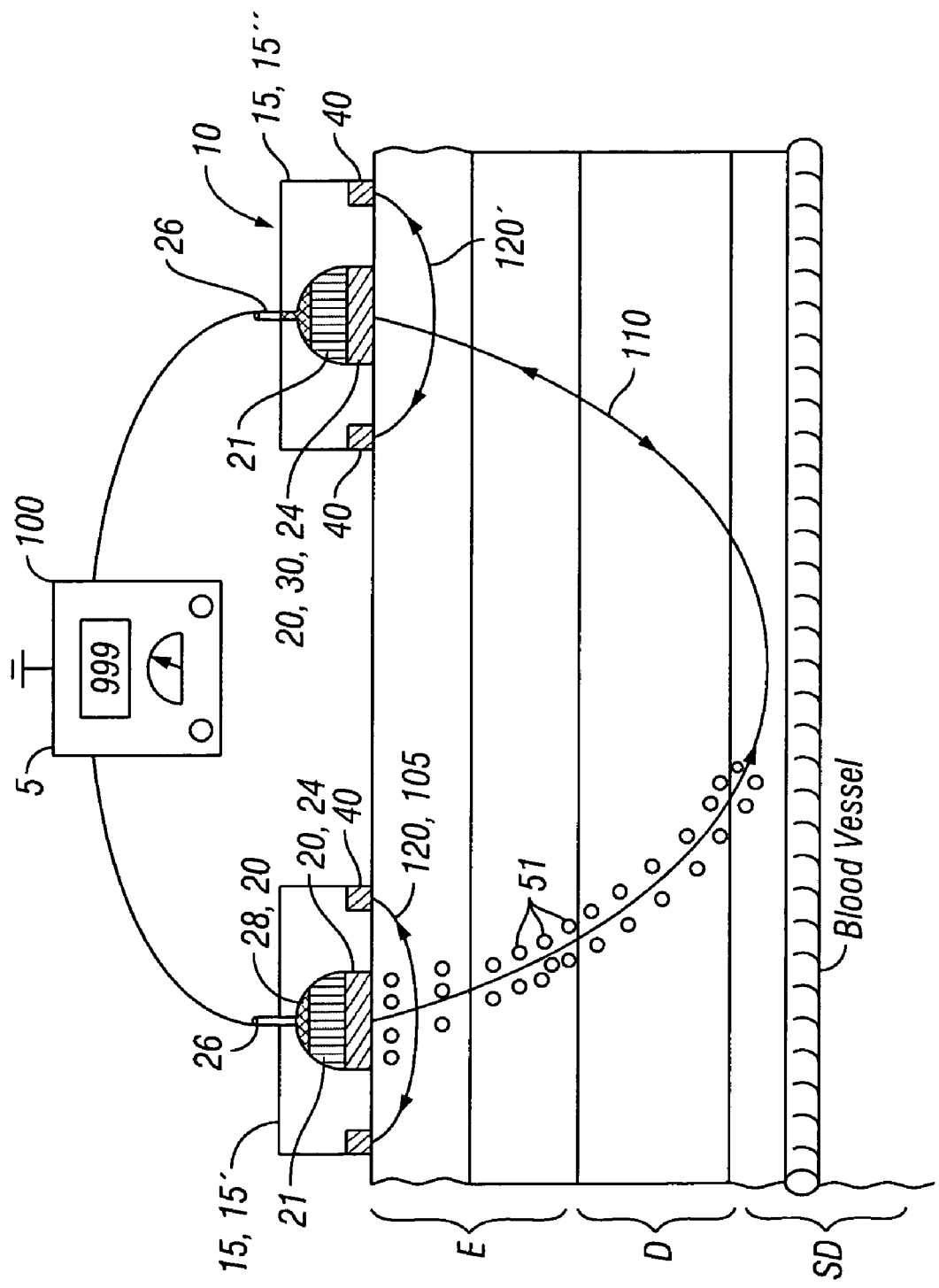
FIG. 2 is a lateral view of an embodiment of a system for the transdermal iontophoretic delivery of various therapeutic agents using delivery and lateral electrodes.

Many embodiments described herein provide a device, system and method for the transdermal iontophoretic delivery of various therapeutic agents. As used herein, the term transdermal delivery refers to the delivery of a compound, such as a drug or other therapeutic agent, through one or more layers of the skin (e.g., epidermis, dermis, etc.). Referring now to FIG. 1, the layers of the skin include the epidermis EP, dermis D and subdermis SD. The upper most layer of the epidermis includes the stratum corneum SC a dead layer of skin (having a thickness of about 10 to 40 μm) and the viable epidermis EP. Transdermal delivery can proceed by one of the three passage ways into the skin, via 1, the sweat pores SP, 2, the hair follicles HF or via permeation 3 through the epidermis E (starting at the stratum corneum) and the dermis.

Iontophoresis is a non-invasive method of propelling high concentrations of a charged substance, known as the active agent, transdermally by repulsive electromotive force using a small electrical charge. The active agent can include a drug or other therapeutic agent. The charge is applied by an electrical power source to an active electrode assembly placed on the skin which contains a similarly charged active agent and a solvent in which it is dissolved. Current flows from the electrode assembly through the skin and then returns by means of a return or counter electrode assembly also placed on the skin. A positively charged electrode assembly, termed the anode will repel a positively charged active agent, or anion, into the skin, while a negatively charged electrode assembly, termed the cathode, will repel a negatively charged active agent, known as a cation into the skin.

Referring now to FIGS. 2-5, an embodiment of a system 5 for the transdermal iontophoretic delivery of a therapeutic agent 51 to a tissue site TS (such as the arm A) on the skin S of patient, comprises at least two electrode assemblies 14 including an active electrode assembly 20 and a return electrode assembly 30; and a power supply 100. Active electrode assembly 20 is used to deliver the therapeutic agent through skin S via current delivered to the skin from power supply 100. Return electrode assembly 30 provides a return path for current to power supply 100. Collectively, the active and return electrode assemblies 20 and 30 comprise a transdermal iontophoretic delivery device 10 also described herein as patch device 10. In embodiments using an alternating current, both electrode assemblies 14 can be configured as active and return electrode assemblies 20 and 30 depending on the direction of current flow. In some cases for sake of brevity, electrode assembly 14, active electrode assembly 20 and/or return electrode assembly 30 will sometimes be referred to as electrode 14, active electrode 20 and return electrode 30.

In many embodiments, the electrode assemblies 14 (e.g., active and return assemblies 20 and 30) comprise or are otherwise disposed on one or more patches 15 configured to be applied to the skin surface. Patches 15 are desirably conformable to a contour CR of a skin surface S and can be fabricated from layers of elastomeric or other flexible polymer material. In some embodiments, two or more electrodes assemblies 14 including active and return electrode assemblies 20 and 30 can be placed on a single patch 15. In other embodiments, system 5 can include separate patches 15 for electrode assemblies 14, for example, a first patch 15' for the active electrode assembly 20 and a second patch 15" for the return electrode assembly 30. In other embodiments, three or more patches 15 can be used so as to have either multiple active electrode assemblies 20 or return electrode assemblies 30 or both. For example, in one embodiment system 5 can comprise three patches 15, including two patches containing active electrode assemblies 20 and a third patch 15 containing a return electrode assembly 30. Other combinations of multiple patches and electrode assemblies are also contemplated, e.g., four patches two for active electrode assemblies 20 and two for return electrode assemblies 30.

Figure 4A:
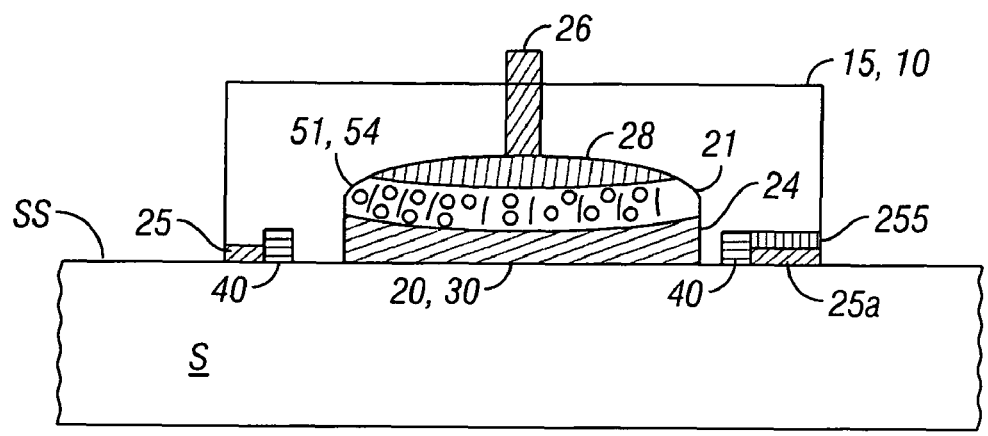
FIGS. 4a and 4b are side and top views showing an embodiment of a skin patch including an active electrode and lateral electrodes.

In many embodiments, active electrode assembly 20 can comprise a reservoir 21 for the therapeutic agent, a tissue contacting porous portion 24 in fluidic communication with the reservoir, an adhesive portion 25 for adhering the assembly to the skin, and an electrical connector 26 for coupling the electrode assembly 20 to an electrical power supply 100 as is shown in the embodiment of FIG. 4a. Reservoir 21 can be sized for the particular dose of therapeutic agent to be delivered.

Tissue contacting portion 24 is also conductive by virtue of being fabricated from conductive porous materials (e.g., conductive fibers) or becomes conductive by becoming wetted with conductive solution 54 (the conductivity being due to agent 51 or various electrolytes added to the solution) and thus functions as an electrode 20. Connector 26 can extend into or otherwise make electrical contact with tissue contacting portion 24. In some embodiments, connector 26 can be coupled to a conductive element 28 positioned within the electrode assembly 20 and coupled to conductive porous portion 24. One or more of conductive element 28, conductive layer 34 (described below) as well as lateral electrodes 40 (also described below) can comprise various conductive materials including stainless steel, carbon, AgCl or other conductive materials known in the art.

Figure 3A:
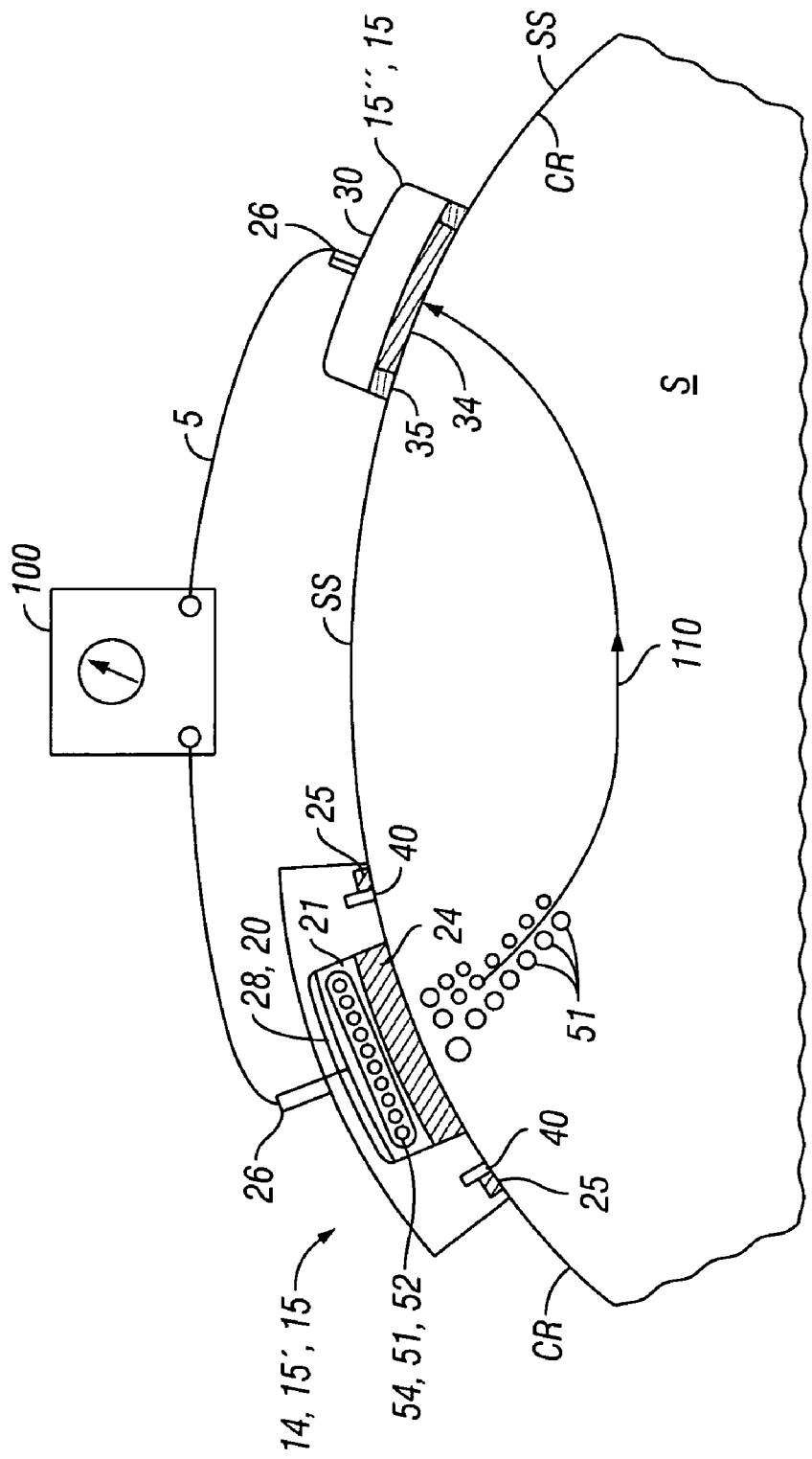
FIG. 3a is a schematic side view showing placement of an embodiment of a transdermal iontophoretic patch device on the surface of the skin, wherein the device comprises an active electrode assembly and a return electrode assembly.
Figure 3B:
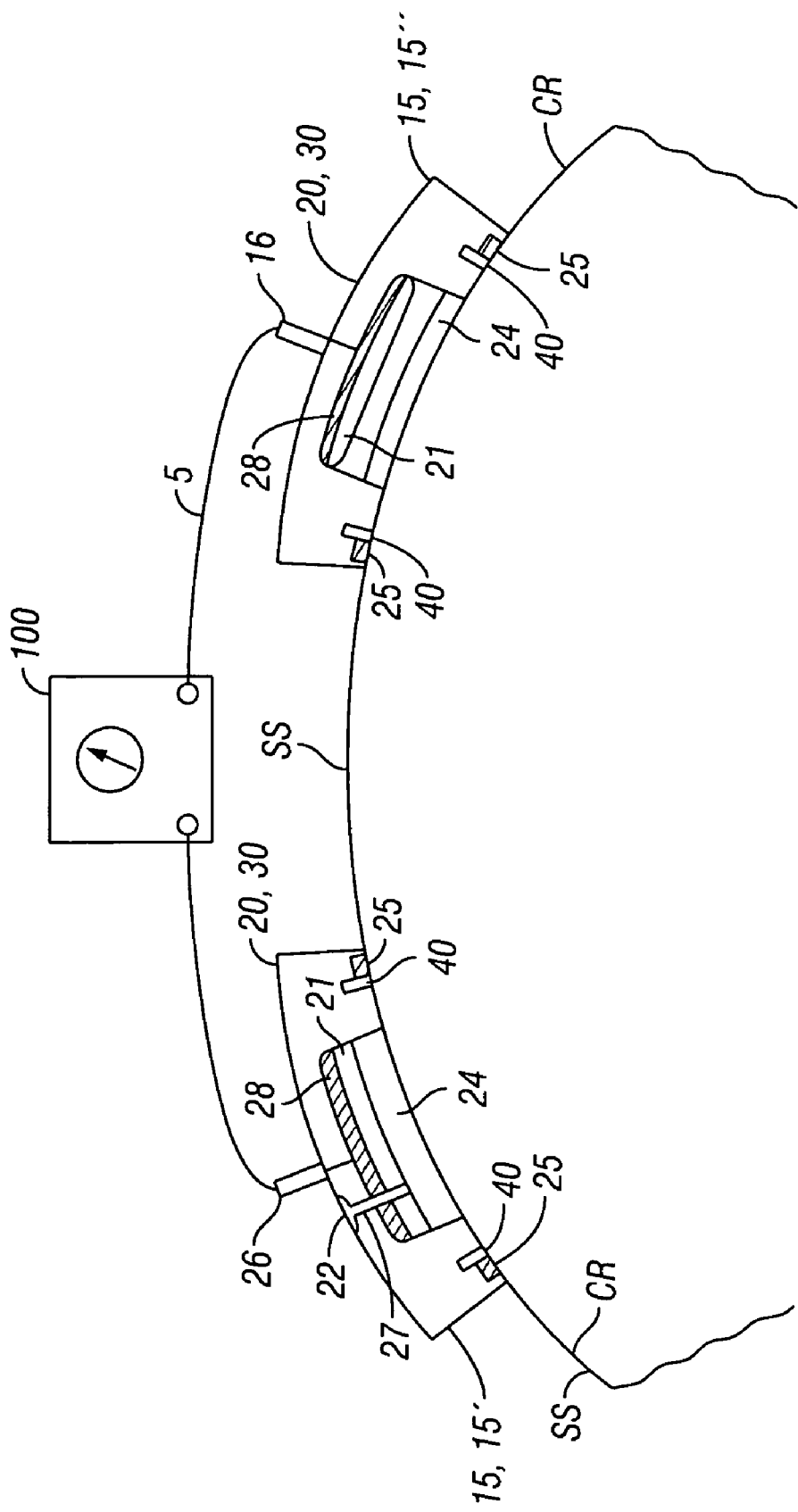
FIG. 3b is a schematic side view showing placement of an embodiment of transdermal iontophoertic patch device on the surface of the skin, wherein the device comprises two active electrode assemblies.

Typically, the therapeutic agent 51 will be dissolved in a therapeutic agent solution 54, also described as therapeutic agent composition which is used to fill reservoir 21. In addition to agent 51, composition 51, solution 54 can include one or more pharmaceutical excipients 52 such as preservatives. The viscosity of the solution 54 can be adjusted to have the solution readily wick from reservoir 21 into porous layer 24. Solution 54 can be preloaded into the reservoir 21 at the factory or can be added by medical personal prior to use through means of a port 22, such as self sealing port allowing injection which is coupled to reservoir 21 via means of a channel 27 as is shown in the embodiment of FIG. 3b The return electrode assembly 30 comprises a tissue contacting conductive layer 34, an adhesive layer 35 and a connector 26 for coupling the electrode assembly to the electrical power source. In many embodiments, the return electrode assembly 30 can have substantially the same elemental configuration as active electrode assembly 20 (e.g., a reservoir 21, conductive tissue contacting layer 24) so as to function as an active electrode assembly as is shown in the embodiment of FIG. 3b.

Figure 4B:
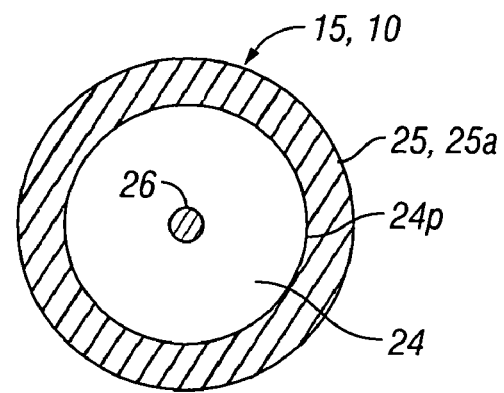
Figure 4C:
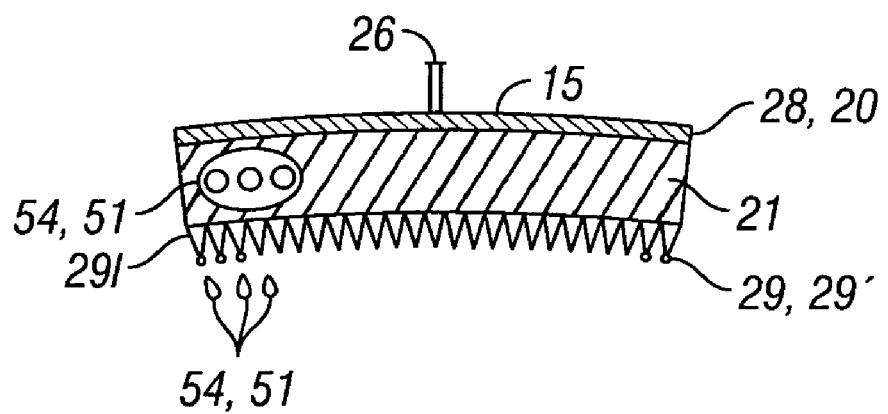
FIG. 4c is a side view showing an embodiment of a skin patch including an active electrode and have a layer of skin penetrating hollow needles for penetrating the stratum corneum and delivering therapeutic agent into the epidermal layer.
Figure 4D:
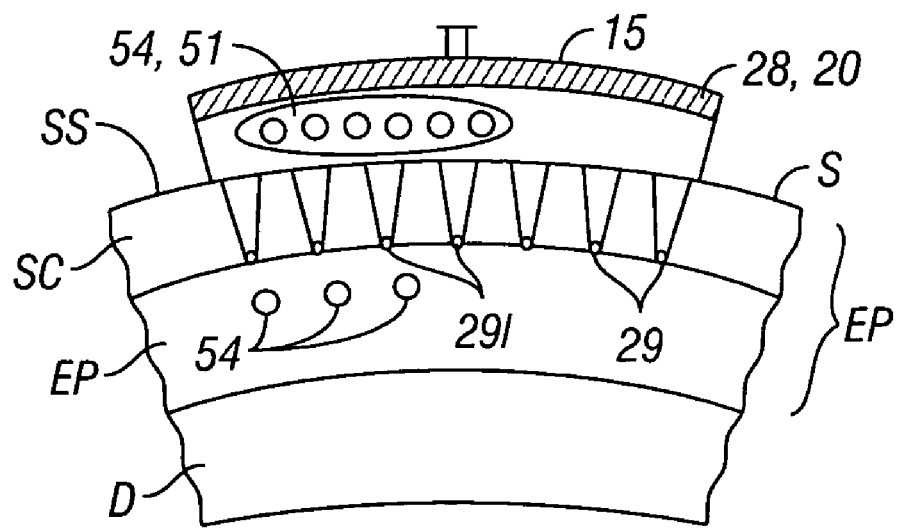
FIG. 4d is a side view showing positioning of the embodiment of the patch of FIG. 4c on the skin surface and it's use for directly delivering therapeutic agent through the hollow needles and into the epidermal layer.

Typically, adhesive portion 25 will surround the perimeter 24p of porous portion 24 as is shown in the embodiment of FIGS. 4a and 4b, though other arrangements are also contemplated. In various embodiments, porous portion 24 can comprise a porous layer 24 that in turn comprises various porous materials including polymers foams, membranes or weaves of polymer fibers known in the art including polyesters, PETs and like materials. Adhesive portion 25 may be attached to porous layer 24 and include various releasable adhesives known in the art. The adhesive portion 25 can comprise an adhesive layer 25a, such as one or more releasable adhesives attached to a substrate layer 25s, which can comprise various hydrogels, polyurethanes, silicones or like polymeric materials. The size and configuration of adhesive portion 25 can be adapted for the particular skin location (e.g., arm vs. leg, amount of hair, etc.) and type of skin (e.g., pediatric vs. geriatric etc, amount of hair, etc.).

In many embodiments, patch 15 also includes one or more pair of electrodes known as lateral electrodes 40. Lateral electrodes 40 are desirably placed on either side of porous portion 24.at a selectable distance from the perimeter 24p of porous portion 24 as is shown in the embodiments of FIGS. 3a-3b and 4a-4b. Electrodes 40 can comprise various conductive materials including metals, graphite, carbon impregnated materials (e.g., fibers), silver chloride and other like materials. In various embodiments, all or a portion of electrode 40 can include an insulative coating so as to be a capacitively coupled electrode that delivers current to the skin via capacitive coupling. Electrodes 40 are also desirably electrically isolated from electrodes 20 and 30 will typically include their own wave form generator circuits described herein.

The lateral electrodes 40 are desirably arranged with respect to porous portion 24 such that they result in a conductive pathway 105 which goes through the skin S underlying portion 24 and is substantially parallel to the skin. As will be described below, embodiments of patch 15 that employ lateral electrodes 40 with delivery electrodes 20, allow for the flow of two currents, a first current 110 and a second current 120. First current, 110 flows between electrodes 20 and 30 and serves to provide an electromotive force which acts to drive the therapeutic agent 51 into and across the layers of the skin S. The second current 120, known as sieving current 120, provides an electromotive force that acts on the therapeutic agent 51 in a direction parallel to the skin surface SS so as to cause oscillation of therapeutic agent 51 in a direction parallel to skin surface SS and/or in a direction substantially non-parallel with the first driving force. This oscillation acts to sieve the therapeutic agent through pathways of lesser or least diffusional resistance in the skin. For embodiments where second patch 15" contains lateral electrodes 40 and is used to deliver therapeutic agent, a third current 120' can be delivered from lateral electrodes on the second patch 15" to also create a electromotive driving force 125 to oscillate the therapeutic agent substantially parallel to the skin surface underneath the second patch 15" and/or in a direction substantially non-parallel with the first driving force.

Figure 5A:
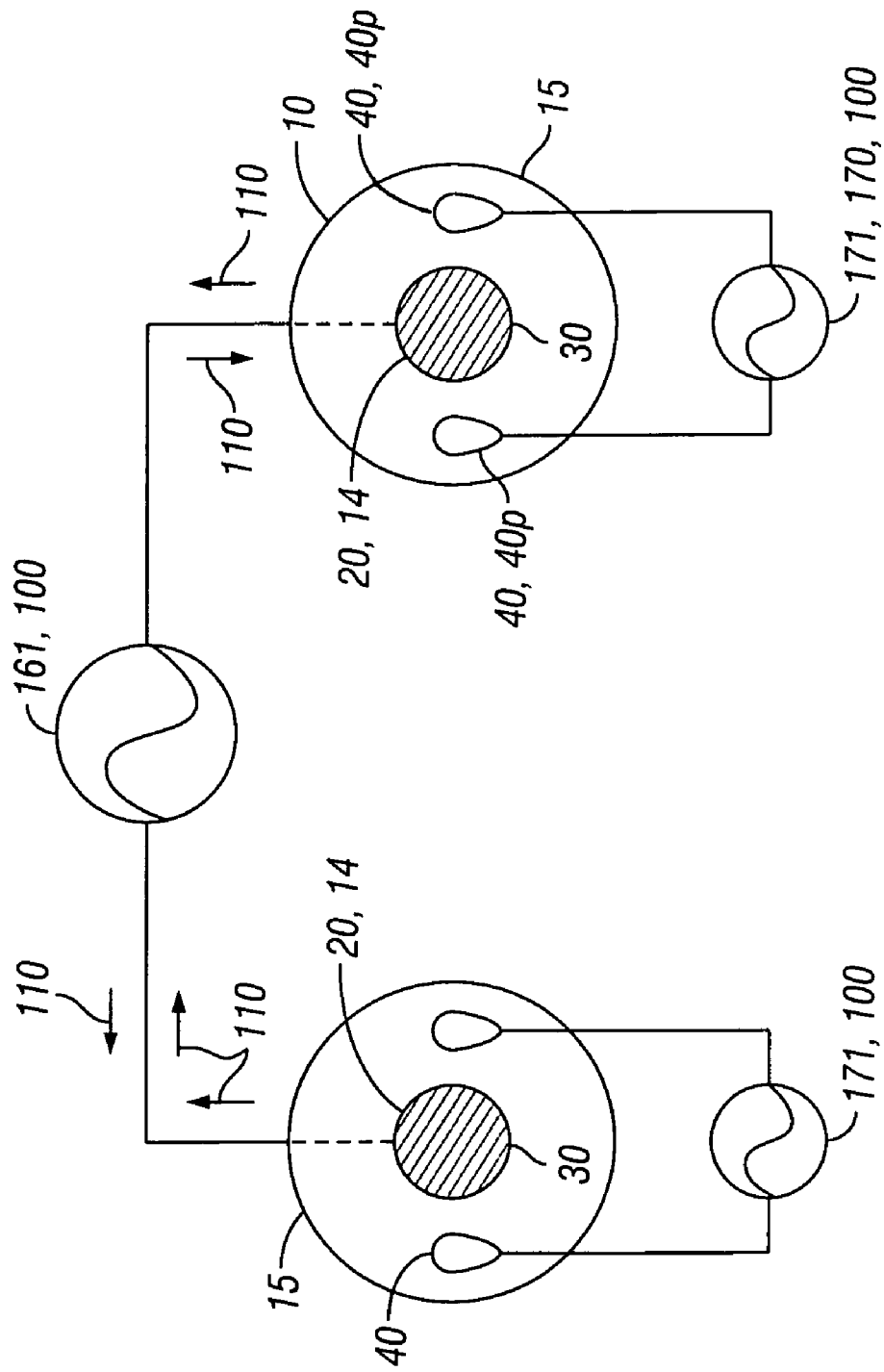
FIG. 5a is a top view showing an embodiment of the invention having two patches, each patch including a delivery electrode and a pair of lateral electrodes.

Several different configurations of lateral electrodes 40 are contemplated by embodiments of the invention. For embodiments employing two or more delivery electrode assemblies 20 (e.g., those embodiments using an AC delivery current), a separate pair 40p of lateral electrodes 40 can be placed on either side of each delivery electrode 20 as is shown in the embodiment of FIG. 5a. In some embodiments two or more delivery electrodes 20 can be positioned on a common patch 15c as is shown in the embodiment of FIG. 5b. In these and related embodiments, a first lateral electrode 41 can be placed on the side of a first delivery electrode 21 and a second lateral electrode 42 can be placed on the opposite side of a second delivery electrode 22 with a third lateral electrode 43 placed in between the first and second delivery electrode 21 and 22. Third lateral electrode 43 serves as a common electrode to electrode 41 and 42. This and related arrangements allows for the flow of a first sieving current 121 between electrodes 41 and 43 and thus through skin underlying first delivery electrode 21 and the flow of a second sieving current 122 between electrodes 42 and 43 and thus through the skin underlying second delivery electrode 22. This arrangement can also be re-configured for use with any number of delivery electrodes 20. In still other embodiments, multiple pairs 40p of lateral electrodes 40 can be positioned with respect to delivery electrodes 20 so as to create oscillations of therapeutic agent 51 in multiple directions with respect to the skin surface to further enhance the sieving effect on the therapeutic agent 51 and thus its transport through the skin. In these single patch embodiments, the patch can have a peanut or other inwardly concave shape so as to be able to bend and flex with movement of the skin surface and thus stay attached to or otherwise in contact with the skin during normal body movement and so continue to deliver currents (e.g., 110, 120, etc.) and the therapeutic agent to the skin. In these and related embodiments, the shape of single or unitary patch 15u can be adapted for the location (e.g., arm vs. a leg) and the size of the patient (e.g., child vs. an adult).

The number and configuration of the lateral electrodes 40 on patch 15 can be selected based on a number of factors. In particular embodiments, the configuration of the lateral electrodes 40 can be selected based on one or more of the following factors: i) the specific therapeutic agent to be delivered (e.g., and iron compound vs. a polypeptide); ii) the skin type and location (e.g., arm vs. leg, pigmented vs. un pigmented); iii) the level of skin hydration; iv) skin thickness; and v) the electrical impedance of the skin. Matrices of these factors can be used to select a configuration of lateral electrodes for particular patient populations, with fine tuning based on the skin of each individual patient.

Referring back to FIGS. 4a and 4b, in some embodiments, patch 15 can contain a layer 29' of hollow needles 29 having a length configured to penetrate into or through the stratum corneum SC but not penetrate so deep so as to make contact with or otherwise stimulate the pain receptive nerve cells of the skin (the "pain receptors") so as to cause appreciable pain to the patient. Further details of this length are described below. The needles lumens 29l have diameter and surface tension (e.g., wettability) configured to allow therapeutic agent solution 54 to pass though the lumen into epidermis EP without having to pressurize the reservoir 21. Needles 29 can be fabricated using various micro machining methods known in the art including various mems-fabrication methods including photolithography based methods. In use, embodiments of patch 15 having needles 29 allow increased amounts of therapeutic agent to be delivered into the skin because the diffussional resistance of the stratum corneum is entirely or substantially bypassed.

Needles 29 are desirably fabricated from a conductive material such as a metal but can also be made from non conductive materials such as various polymers. They may also be slightly flexible to allow for positioning and conformance to the contour CR of a skin surface SS. For conductive embodiments, the needles can be arranged in pattern which provides for a substantially uniform current density delivered to the skin over that pattern. In use, such embodiments, can provide for a more uniform delivery of therapeutic agent over the tissue contacting layer of the patch 24 (in the case layer 29') and also reduce any heating or even over heating of tissue which may be attributable to edge effects or other uneven concentration of current density due to any material or morphological non uniformities (e.g., pitting, etc.) in the tissue contacting layer 24. These two attributes in turn can also increase the transdermal delivery of therapeutic agent into the skin via use of iontophoresis.

Figure 6:
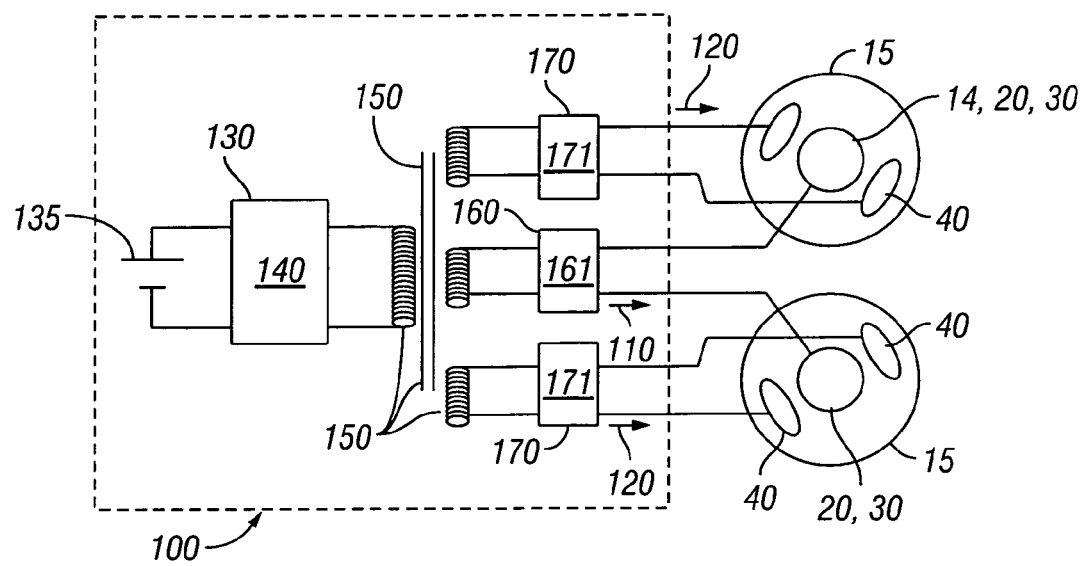
FIG. 6 is a schematic view showing an embodiment of power control circuitry for use with embodiments of the transdermal iontophoretic delivery system.

Referring now to FIG. 6, power supply 100 can include power control circuitry 130 also described as controller 130 which comprises a first controller 140 coupled to a power source 135 (e.g., either a battery or an AC source) and an electrical isolation means 150 coupling controller 140 to one or more controllers 160 for controlling power to delivery electrodes 30 and one or more controllers 170 for controlling power to lateral electrodes 40. One or more of controllers 140, 160 and 170 can comprise a microprocessor and/or state device for controlling one or more functions of the power supply 100; memory resources for storing one or more software algorithms and data used by the microprocessor; a dc-dc converter for modifying voltage from the battery; a dc-ac converter for supplying AC power to one or more devices 10 and electrodes 14; and a multiplexor or power rail for supplying separate power/electrical signals to electrodes 30 or 40. Controllers 160 and 170 can also comprise or be coupled to waveform generation circuits 161 and 171 for generating waveforms for currents 110 and 120 which are also described as signal 110 and 120.

In various embodiments, isolation means 150 can comprise an isolation transformer, an optical isolation device or other electrical isolation device known in the art. These and related embodiments of circuitry 130 allow electrodes 30 and 40 to be electrically isolated from each other and also allow for independent control of the signal/electrical characteristics at each electrode, including voltage, current and frequency. So for example, a first current 110 flowing between electrodes 30 can have a first voltage and frequency, while a current 120 flowing between electrodes 40 can have a second voltage and frequency.

In various embodiments, the power supply 100 can include various features to facilitate use by medical personnel both in a hospital setting and in the field. For example, the power supply can include or be configured to be coupled to a bar reader (not shown) for reading bar codes positioned on one or more of electrode assemblies 14, patches 15 or power supply 100. In exemplary method of using a bar code reader, the patient or medical care provider could scan the code on a patch 15 so to ascertain the dose and type of therapeutic agent as well as the lot number, expiration date and like production data. Further description of embodiments of power supply 100 including controller 130 is found in U.S. Provisional Patent Application Ser. No. 61/214,642 which is incorporated herein by reference in its entirety.

Figure 7:
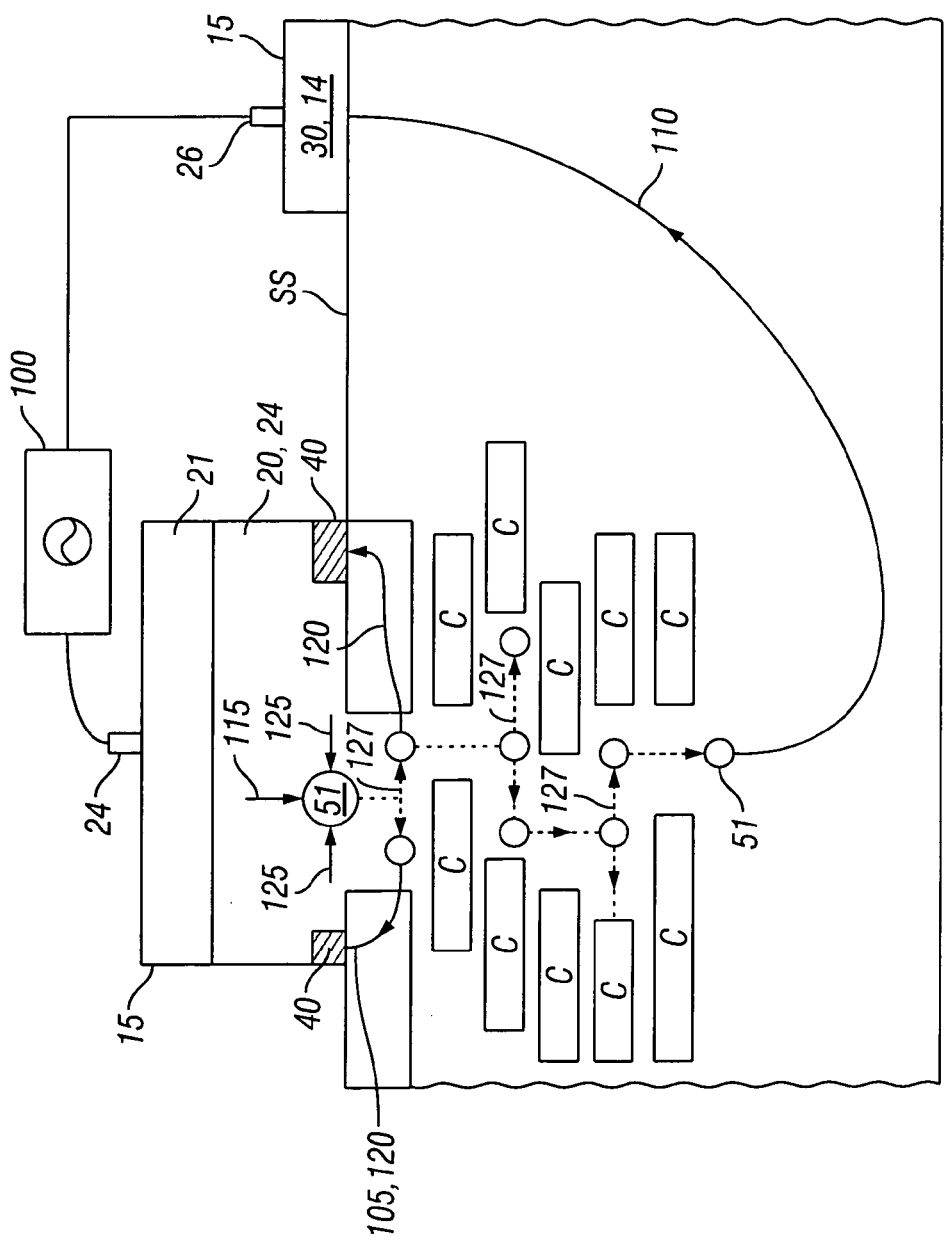
FIG. 7 is a cross sectional view of the skin illustrating the forces and motion of the therapeutic agent induced by the use of a transdermal current and sieving current.
Figure 8:
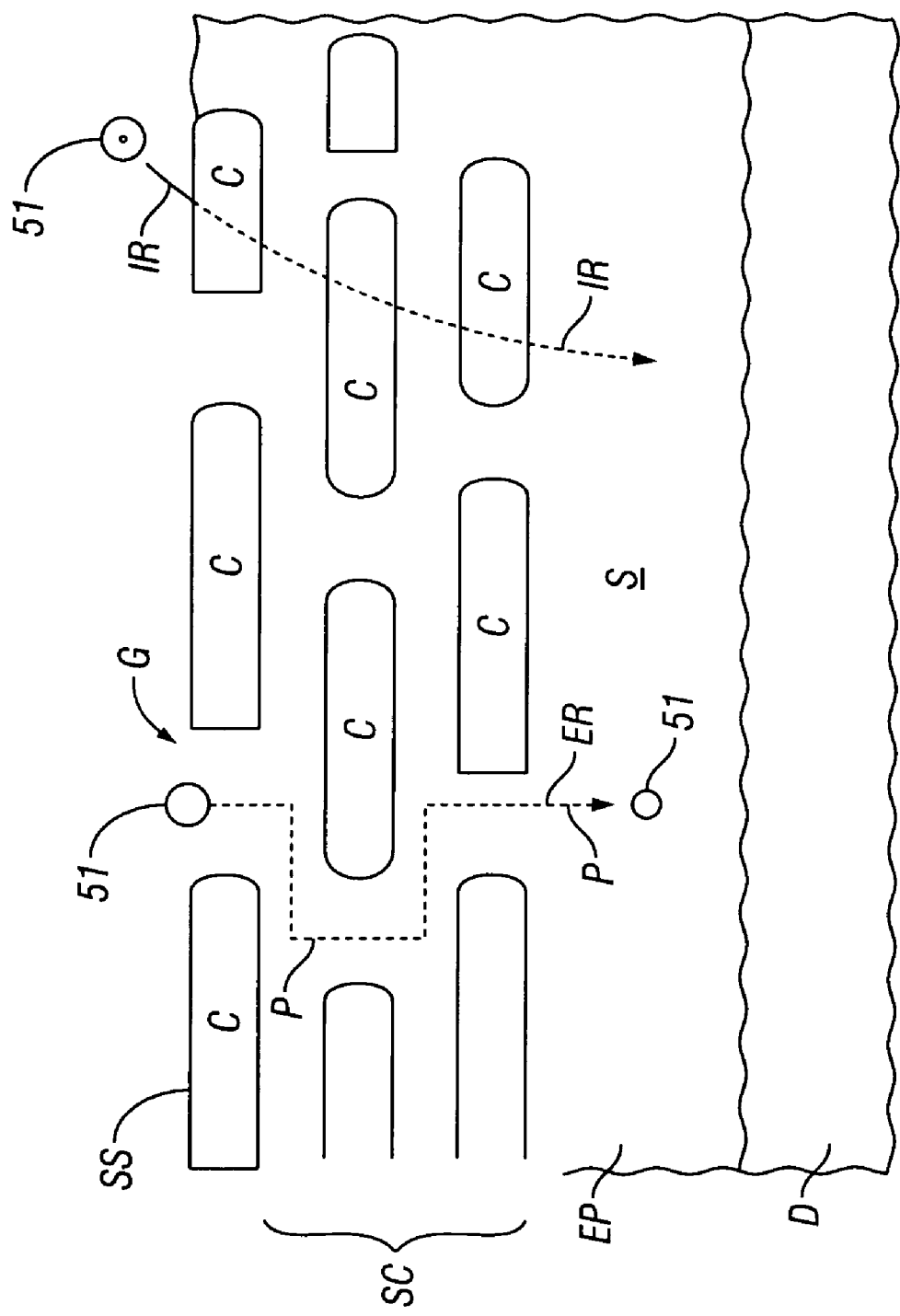
FIG. 8 is a cross sectional view of the skin illustrating use of oscillating motion of the therapeutic agent to sieve the therapeutic agent through the skin.

Referring now to FIGS. 7-8, a discussion will be presented on various embodiments of the invention for enhancing transdermal iontophoretic delivery of therapeutic compounds using a sieving current. As discussed herein, many embodiments of the invention employ a first current 110 flowing between delivery electrodes 30, also described herein as a "transdermal current" and a second current also described herein as a "sieving current" flowing between lateral electrodes 40. The first or transdermal current 110 flows between electrodes 30 and creates a first electromotive driving force 115 acting in a direction substantially orthogonal to the skin surface SS to transport the therapeutic agent into the skin. The second or sieving current 120 flows between the lateral electrodes 40 and creates a second electromotive driving force 125 acting substantially parallel to the skin surface SS to oscillate therapeutic agent 51 in an oscillatory path 127 (e.g., back and forth) within the skin in a direction substantially parallel to the skin surface SS as is shown in the embodiment of FIG. 7. Oscillatory path 127 also includes directions which are substantially non-parallel with the direction of first driving force 115. As a result of the application of forces 115 and 125, as the therapeutic agent is pulled/propelled into the skin from the first force 115, it is also oscillated back and forth horizontally within the skin in a direction substantially parallel to the skin surface SS and/or in a direction non-parallel to the direction of first force 115. The net effect is that the agent 51 is effectively sieved through the skin so as to find and travel through gaps G in the skin, (typically in the stratum corneum) and other pathways P of least diffusional resistance in the skin as is shown in the embodiment of FIG. 8. Because the diffusional resistance is less through pathways P, the rate and total amount of delivery of therapeutic agent 51 can thus be enhanced.

As is shown in FIG. 8, the pathways of transport of therapeutic agent 51 through the skin can include intracellular pathways or routes IR (going through one or more cells C) and extracellular pathways or routes ER such as gaps G. In various applications of the above methods the pathways P of least diffusional resistance in the skin may include various extracellular routes ER including gaps G in the stratum corneum layer of the skin, pores and other openings in the skin. They may also include intracellular routes IR including areas of skin having increased hydration and/or reduced thickness.

Any appropriate current may be applied to the skin using the above methods, including an alternating current or a direct current and combinations thereof. Typically, the second current or sieving current 120 is an alternating current so as to produce the oscillation motion of the therapeutic agent. In many embodiments, an alternating current is used for both the first current and the second currents 110 and 120.

The characteristics of one or of both of currents 110 and 120 (e.g., frequency, amplitude) can be adjusted to enhance the delivery of therapeutic agent 51 through the skin by enhancing the sieving effect. The adjustment can be made depending on one or more adjustment factors ("the adjustment factors"). Such factors can include the frequency of the first current, the charge to mass ratio of the therapeutic agent, the conductive properties of the skin (e.g., impedance) and the type and thickness of the skin subjacent the patch(s). The skin type can relate to one or more of the skin location (e.g., arm vs. finger) and the skin age (e.g., neonatal, pediatric or geriatric), amount of pigmentation and degree of sun-damage. Higher sieving current frequencies can be used for thicker, less hydrated skin.

In certain embodiments, the frequency of the second current 120 can be adjusted to be substantially larger than the frequency of the first current. For example, the frequency of the first current may be in the range from about 1 to about 100 Hz, and the frequency of the second current may be in the range from about 50 to 1000 Hz with specific embodiments of 100, 250, 500 and 750 Hz. Specific embodiments of the oscillophoretic current frequency can include 100, 250, 500 and 750 Hz.

One or both of the first or second currents can be in the range of 0.05 to 0.8 ma, with specific embodiments of 0.1, 0.2, 0.3 and 0.4 ma with other values also contemplated. Also, the voltages for one or both of currents 110 and 120 can be in the range 1-14 volts with specific embodiments of 5, 6, 7, 8, 9, 10, 11, 12 or 13 volts. In particular embodiments, one or both of signals 110 and 120 can be current controlled (e.g., by controller 130, 140, 160 or 170) so that current is fixed and the voltage will vary. In these and related embodiments, the current can be controlled in the range from about 10 μa to 4 ma.

In certain embodiments, first current 110 can be larger than the second current 120 either in the current value or voltage so as to have the value of force 115 exceed the value of force 125. The value of either of the current or voltage of current 110 can between 20 to 500% that of the corresponding value for current 120 with specific values of 25, 50, 100, 200, 250, 400 and 400%. For example, in one embodiment, first current 110 can have a value of 4 ma and the second current can have a value of 2 ma so that current 110 is 200% that of current 120. Also first current 110 can have a voltage of 4 volts and the second current 120 can have a voltage of 2 volts.

In some embodiments, the second current 120 can be delivered by means of capacitive coupling to skin rather than through delivery of a farradaic current. In these and related embodiments electrodes 40 can be capacitively coupled electrodes that comprise conductive materials surface coated with a dielectric such that no farradaic current flows from the electrode surface to the tissue. Instead, current flows by means of capacitively coupling of the electrodes to the skin surface. In these and related embodiments the frequency of the first current can be in the range of 50 Hz, to 100 kHz with a more preferred range of 50 to 1000 Hz.

Various embodiments of the invention also provide methods for the iontophoretic transdermal delivery of a therapeutic agent using one or more embodiments of system 5 and patch 10. Exemplary embodiments of such a method comprises delivering a first current to the skin to create a first electromotive driving force to transport the therapeutic agent into the skin, and delivering a second current to the skin to create a second electromotive driving force to oscillate the therapeutic agent in a direction substantially parallel to the skin surface. The therapeutic agent is transported across the skin using the first electromotive driving force to propel the agent into the skin, and the second electromotive driving force to oscillate the therapeutic agent substantially parallel to the skin surface (and/or in a direction substantially non-parallel to the direction of the first driving force) so that it is sieved through pathways of least diffusional resistance in the skin. The pathways of least diffusional resistance can include areas of greater hydration, reduced thickness, pores (e.g., sweat pores), hair follicles or gaps in the skin including gaps in the stratum corneum layer of the dermis.

Various embodiments of the invention contemplate transdermal delivery of therapeutic agents on a wide variety of iontophoretic transdermal delivery platforms for the delivery of a wide variety of therapeutic agents. These include single patch, double patch and other multiple patch embodiments using AC or DC current or combinations thereof. Embodiments of the invention can also be configured for delivery of a therapeutic agent using a combination of passive and active diffusion (e.g., passive and iontophoretic transdermal delivery). Further description of suitable iontophoretic transdermal delivery platforms and currents, including combination currents is found in U.S. Provisional Patent Application Ser. No. 61/214,642.

In other embodiments of methods for enhancing the delivery of a therapeutic agent using transdermal iontophoretic delivery, prior to the delivery of one or more currents 110 and 120, skin S can be pretreated so as create gaps G in the stratum corneum SC to reduce the diffusional resistance of the stratum corneum SC. In one or more embodiments, this can be achieved through the use of one more micro-needles or other tissue penetrating elements which have a length configured such that they create gaps or holes G in the stratum corneum but do not penetrate deep enough into the skin to cause any appreciable amounts of pain to the patient. In use, such embodiments create gaps G at control depth into the skin to on the one hand enhance iontophoretic transdermal delivery into the skin, but on the other not to go so deep enough to as to make contact with or otherwise stimulate the pain receptive nerve cells of the skin (the "pain receptors") so as to cause appreciable pain to the patient.

In particular embodiments, the depth of penetration of the micro needles or other tissue penetration device can be in the range of 5 to 100 µm, more preferably 10 to 50 µm, and still more preferably 20 to 40 µm, with specific embodiments of 5, 10, 20, 30, 40, 50, 60, 70, 80 and 90 µm. Preferably, the penetration depth is contained within the stratum corneum, but may go deeper into the epidermal layer. In various embodiments, deeper penetration depths can be used to obtain increased amounts of delivery of the therapeutic agent.

The penetration depth can be adjusted depending upon the i) pain perception of the patient, and/or ii) the thickness of the stratum corneum at the particular skin site for a particular patient. The thickness of the stratum corneum can be measured by taking a skin sample an observing the sample under a micro-scope, or non-invasively using various techniques including optical, impedance, infrared and other thermal methods and other methods known in the art.

In an embodiment of a method for creating gaps in the skin using the above approach, a patch containing a layer of micro-needles or tissue penetrating elements is applied to the skin prior to the application of patch 15, so as to create a plurality of new gaps G over the target skin site. The tissue penetrating patch is then removed leaving the plurality of exposed open gaps G over the target skin site. As an alternative to the patch a hand held tool containing layer of micro-needles on its distal end can also be used by applying the distal end to the skin surface. The tool may include various stops or other fittings for controlling the depth of penetration.

After removal of the tissue penetrating patch or tool, patches 15 containing delivery electrodes 20 are then applied over the target site and current 110 is applied to the skin as described herein to propel therapeutic agent 51 into skin through the plurality of gaps G. As described herein, because the diffusional resistance is greatly reduced by the plurality of newly created gaps G, the amount of therapeutic agent 51 delivered is substantially enhanced.

In other embodiments the transdermal delivery of therapeutic agent 51 can be enhanced through use of patches 15 which contain a layer 29' of hollow microneedles 29 on their tissue contacting surface. Needles 29 have lumens 29l and have a depth selected to project through the stratum corneum into the epidermis but not go so deep as to substantially stimulate the pain receptors of the skin. In these and related embodiments, therapeutic agent solution 54 including therapeutic agent 51 flows through the needle lumens 29l into the epidermal layer EP where it is carried deeper into the skin by the electromotive propelling forces 115 described herein. In use embodiments of patch 15 employing hollow needles 29 can substantially enhance the amount of therapeutic agent delivered into the skin because the diffusional resistance of the stratum corneum is substantially or entirely bypassed. In particular embodiments, the delivery of therapeutic agent 51 can be further enhanced by applying a a fluidic pressure to reservoir 21 and in turn to lumens 29l through a pressure source such as a pump or a compressed gas source. Fluidic pressure can also be developed by slight heating of solution 54 from current 110.

As described above, embodiments of the invention can be adapted for use with a wide variety of therapeutic agents and other compounds. Such therapeutic agents 51 can include without limitation the following: iron compounds, antibiotics (e.g., penicillin, ampicillin, erythromycin, ciprofloxacin, vancomycin, etc), antibodies, proteins, polypeptides, insulin and other glucose regulating compounds, various anti-diarrheal drugs (e.g., Loperamide oxide) various chemotherapeutic agents (e.g., doxorubicin), various vaccines (e.g., diphtheria, cholera, tetanus, flu, measles and polio vaccines, including vaccines in the form of de-activated pathogens as well as antibodies), and various hormones having birth control properties (e.g., estrogen and progesterone as well as combinations thereof). The therapeutic agents can also include various pro-drugs which are metabolized into their active form once released into the body. Suitable pro-drugs can include anti-viral nucleoside analogs, lipid-lowering statins, antibody-directed/gene-directed enzyme prodrugs for chemotherapy, etoposide phosphate, valganciclovir and fosamprenavir. These therapeutic agents can be lyophilized, including vaccines, antibodies, proteins and peptides.

In exemplary method embodiments of the invention, the therapeutic agent composition can comprise iron containing compounds for the treatment of iron deficient anemia or other related condition. For example, the iron compound may be a chelated form of iron such as ferric pyrophosphate, ferric ammonium sulfate, and/or one or more ferrous salts, such as ferric chloride or ferrous chloride. In embodiments in which a chelated iron compound is employed (as described below), the method can be adapted so that the iron compound is transported without producing a substantial cosmetic change to the skin, such as a tattoo. Further description on the use of iontophoretic transdermal delivery methods for the delivery of chelated iron and other compounds is found in U.S. Provisional Patent Application Ser. No. 61/214,642.

Other iron compounds and salts are also contemplated and include iron dextran, iron carboxymaltose, iron sucrose, and complexes of iron with gluconate, nitrilotriacetate or succinate. The composition can also comprise one or more preservatives, such as ascorbic acid, to preserve the charge/ionic state of the ferrous salt (having a +2 charge state) to prevent it from converting to a ferric salt (having a +3 charge state). For embodiments using ferrous chloride, the therapeutic solution can be mixed to have a concentration in the range from about 200 to 1000 mg/ml, with specific embodiments of 300, 400, 500 and 750 mg/ml. Related concentrations are also contemplated for other iron salts.

In various embodiments, the therapeutic composition can comprise a chelated complex which comprises a therapeutic agent that is electrostaticaly or otherwise bound to a chelating agent. The chelated complex can be delivered to the skin and underlying tissue using the iontophoretic transdermal methods described herein. This can include applying a patch containing the chelated complex dissolved in solution and then applying current to drive the complex into the skin and underlying tissue as described herein. Suitable chelated iron complexes include ferric pyrophosphate, ferric ammonium citrate and related iron salts. Other suitable chelated iron complexes can include ferrous edetate, ferrous ethylenediamineedetate and ferrous ethylenediaminesuccinate.

In other exemplary method embodiments, methods of the invention can be configured for the transdermal delivery of various incretins proteins including glucagon like peptide (GLP) molecules such as GLP-1 and related molecules having substantial homology with GLP-1 (GLP-1 homologs) such as exindin 4. Such GLP molecules and their homologs can be delivered in dosages for the treatment of one or more forms of diabetes and related conditions. The particular dose can be developed using dose response curve methods known in the art. Further details of exindin 4 and other GLP-1 homologs are described in the paper by B. Furman, "Current and future incretin-based therapies for the treatment of diabetes", Pharmaceutical Journal (Vol 282), May 2, 2009 which is incorporated by reference herein in its entirety. In particular embodiments, the rate of transdermal delivery of such incretin molecules can be titrated based upon measurement of blood glucose or other physiological indicators or correlates of blood glucose levels (e.g., glycosylated hemoglobin, metabolic rate, transdermal temperature gradients, etc.). In still other embodiments, various methods of the invention can be used for the transdermal delivery of LHRH as well as LHRH homologs and agonists for use in birth control as well as use in various cancer therapies such as prostate, breast, etc.

The amount or dose of the respective therapeutic agent(s) can be determined based on the condition to be treated (e.g., anemia, diabetes, etc.) and the patient's weight, age etc. Also, dosages can be based on known therapeutically effective doses for a particular condition that are delivered orally, intravenously, intramuscularly or by other delivery means (e.g., intranasally, inhalation, etc.) with adjustment for different absorption/uptake of the known method (e.g., in the case of orally delivered iron compounds). For example, in the case of orally delivered iron compounds (e.g., ferrous sulfate) for the treatment of anemia, typically about 50 mg of iron are delivered, of which only about 10 to 25 mg are actually absorbed into the blood stream. Accordingly, the dose of iron can be in the range of about 10 to 25 mg or 10 to 50 mg. Additionally, in particular embodiments, dose response curves can be developed for the transdermal iontophoretic delivery of particular therapeutic agents using known pharmacological methods. Again, adjustment can be made for the weight and age of the patient as well as their particular condition, e.g., partum induced anemia.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the iontophoretic patch can be modified in size, shape and dose of therapeutic agent for different medical conditions, different tissue sites as well as for various pediatric applications. Additionally, the delivery and sieving currents can also be modified for skin type, therapeutic agent dose, as well as various pediatric applications. Further, in addition to using a sieving current for transdermal delivery, in various embodiments a sieving current can be adapted for enhancing rates of extraction of various biochemical analytes, which in particular embodiments can include glucose, glycosylated hemoglobin and other like compounds.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for the iontophoretic transdermal delivery of a therapeutic agent to a patient in need thereof, the method comprising:
    applying a first and second patch to the skin of the patient, the first patch comprising a delivery electrode, a therapeutic agent and two lateral electrodes, the second patch comprising at least a delivery electrode;
    delivering a first current to the skin, the first current flowing between the delivery electrodes, the first current creating a first electromotive driving force to transport the therapeutic agent into the skin;
    delivering a second current to the skin, the second current flowing between the lateral electrodes of the first patch; the second current creating a second electromotive driving force to oscillate the therapeutic agent in a direction substantially parallel to a surface of the skin; and
    transporting the therapeutic agent across the skin using the first electromotive driving force to propel the agent into the skin, and the second electromotive driving force to oscillate the agent substantially parallel to the surface of the skin so that the agent is sieved through pathways of least diffusional resistance in the skin.

2. The method of claim 1, wherein the pathways of least diffusional resistance comprise gaps in the skin.

3. The method of claim 2, wherein the gaps are in the stratum corneum layer of the skin.

4. The method of claim 1, wherein the therapeutic agent is delivered to a sub-dermal tissue layer.

5. The method of claim 1, wherein the second current is an alternating current.

6. The method of claim 5, wherein the first current is an alternating current.

7. The method of claim 6, wherein the frequency of the second current is substantially larger than the frequency of the first current.

8. The method of claim 6, wherein the frequency of the first current is in the range from about 1 to about 100 Hz.

9. The method of claim 5, wherein the frequency of the second current is in the range from about 50 to 500 Hz.

10. The method of claim 1, wherein the second patch includes lateral electrodes, the method further comprising:
    delivering a third current to the skin, the third current flowing between the lateral electrodes of the second patch; the third current creating a third electromotive driving force which acts to oscillate the therapeutic agent in a direction substantially parallel to the skin surface.

11. The method of claim 10, wherein the third current is an alternating current.

12. The method of claim 1, wherein the therapeutic agent comprises iron.

13. The method of claim 12, wherein the iron is in the form of an iron compound, an iron salt, ferrous chloride or ferric chloride.

14. The method of claim 1, wherein the therapeutic agent is a chelated iron compound, ferric pyrophosphate or ferric ammonium citrate.

15. The method of claim 14, wherein the chelated iron compound is transported without producing a substantial cosmetic change to the skin.

16. The method of claim 15, wherein the cosmetic change is a tattoo.

17. A method for the iontophoretic transdermal delivery of a therapeutic agent to a patient in need thereof, the method comprising:
    delivering a first current to the skin of the patient to create a first electromotive driving force to transport the therapeutic agent into the skin;
    delivering a second current to the skin to create a second electromotive driving force to oscillate the therapeutic agent in a direction substantially parallel to a surface of the skin; and
    transporting the therapeutic agent across the skin using the first electromotive driving force to propel the agent into the skin, and the second electromotive driving force to oscillate the therapeutic agent substantially parallel to the surface of the skin so that the therapeutic agent is sieved through pathways of least diffusional resistance in the skin.

18. The method of claim 17, wherein the pathways of least diffusional resistance comprise gaps in the skin.

19. The method of claim 18, wherein the gaps are in the stratum corneum layer of the skin.

20. A method for the iontophoretic transdermal delivery of a therapeutic agent to a patient in need thereof, the method comprising:
   delivering a first current to the skin of the patient to create a first electromotive driving force to transport the therapeutic agent into the skin;
   delivering a second current to the skin to create a second electromotive driving force to oscillate the therapeutic agent in a direction substantially non-parallel to the first electromotive driving force; and
   transporting the therapeutic agent across the skin using the first electromotive driving force to propel the agent into the skin, and the second electromotive driving force to oscillate the therapeutic agent in a direction substantially non-parallel to the first electromotive driving force so that the therapeutic agent is sieved through pathways of least diffusional resistance in the skin.

21. The method of claim 20, wherein the first force acts in a direction substantially orthogonal to the surface of the skin to transport the therapeutic agent to the skin.

22. The method of claim 20, wherein the second force acts to oscillate the therapeutic agent in a direction substantially parallel to the surface of the skin.

* * * * *